United States Patent [19]
Darsow

[11] Patent Number: 5,874,648
[45] Date of Patent: Feb. 23, 1999

[54] PROCESS FOR PREPARING ISOCAMPHYLCYCLOHEXANOLS

[75] Inventor: Gerhard Darsow, Krefeld, Germany

[73] Assignee: Bayer Aktiengesellschaft, Leverkusen, Germany

[21] Appl. No.: 928,103

[22] Filed: Sep. 12, 1997

[30] Foreign Application Priority Data

Sep. 19, 1996 [DE] Germany .......... 196 38 300.5

[51] Int. Cl.$^6$ .................................. C07C 35/22
[52] U.S. Cl. ............................................ 568/820
[58] Field of Search ................... 568/822, 832, 568/835, 820

[56] References Cited

U.S. PATENT DOCUMENTS

| | | |
|---|---|---|
| 4,014,944 | 3/1977 | Hall et al. . |
| 4,104,203 | 8/1978 | Hall et al. . |
| 4,245,124 | 1/1981 | Bauer et al. . |

OTHER PUBLICATIONS

F.M. Nelson and F.T. Eggersten, Analyt. Chem. 30 (1958) pp. 1387–1390.

*Primary Examiner*—Michael L. Shippen
*Attorney, Agent, or Firm*—Sprung Kramer Schaefer & Briscoe

[57] ABSTRACT

To prepare isocamphylcyclohexanols by hydrogenating compounds containing the carbon skeleton of the isocamphylguaiacols or isocamphylphenols, oxygen-free and support-free molded bodies disposed in a fixed bed and made of compacted powders of the elements of the ferrous subgroup of group VIII of the periodic system or their mutual alloys or their alloys with elements of group VIB are used as catalysts; in addition, hydrogenationally inert elements may be present. The molded bodies have a compressive strength of 20 to 250N and an internal surface area of 10 to 90 $m^2/g$.

20 Claims, No Drawings

PROCESS FOR PREPARING ISOCAMPHYLCYCLOHEXANOLS

The invention relates to a novel, continuous process for preparing from compounds having the carbon skeleton of the isocamphylguaiacols or isocamphylphenols by hydrogenation with hydrogen using catalysts.

BACKGROUND OF THE INVENTION

Isocamphylcyclohexanols are constituents of the industrially produced sandalwood perfumes, which are composed of synthetic mixtures of various terpencyclohexanol isomers. Industrial sandalwood perfumes replace natural sandalwood oil in soaps, cosmetic products and perfume compounds.

As starting compounds for the isocamphylcyclohexanols, for example, the isocamphylguaiacols can be prepared in a known manner by reacting camphene with guaiacol with the aid of acidic catalysts, for example boron trifluoride and acetic acid; the isocamphylguaiacols are then converted into the isocamphylcyclohexanols by hydrogenation of the aromatic nucleus and cleavage of the methoxy group.

The reactions proceed according to the following equation:

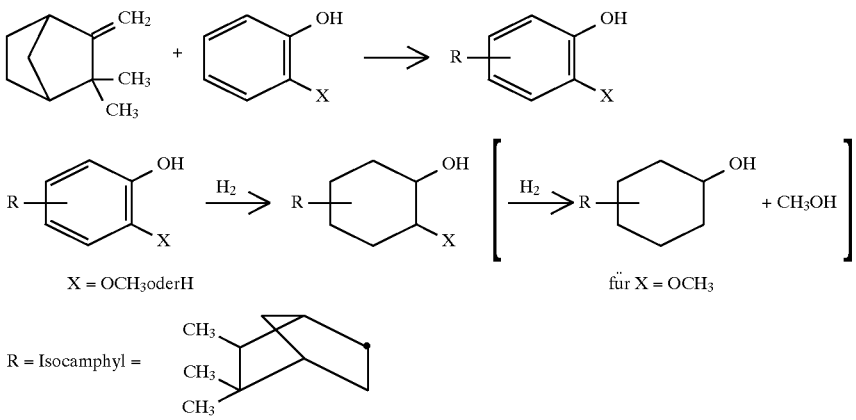

It is already known to hydrogenate alkylation mixtures of camphene and catechol (U.S. Pat. No. 4,014,944) or camphene and guaiacol (DE-A 2 921 139) with hydrogen over Raney nickel to form the desired isocamphylcyclohexanols.

Without exception, these processes of the prior art proceed discontinuously using powdered catalysts by the suspension process.

In the case of powdered catalysts, the following difficulties exist (1) to activate said catalysts in a controlled and uniform manner, (2) to circulate powdered catalysts with the aid of special sludge pumps and (3) to separate powdered catalysts quantitatively from the reaction product. Sludge pumps are, after all, subject to a high mechanical loading. The quantitative removal of powdered catalysts is furthermore expensive because it requires a coarse filtration and a fine filtration using equipment with switching facility. Furthermore there is a great risk that the catalysts quickly lose their activity as a result of these additional operations and therefore furthermore cause high catalyst consumptions. In addition, powdered catalysts can only be loaded to a limited extent and can be freed from the reaction products only with difficulty, which makes their working-up difficult.

The object was therefore to prepare highly loadable, acid-resistant and long-life catalysts for preparing isocamphylcyclohexanols which catalysts should be free of complicated support systems and therefore capable of being worked up again.

SUMMARY OF THE INVENTION

Surprisingly, the problem described can be solved with the aid of support-free fixed-bed catalysts which are present as compacted molded bodies which are produced from metal powders or alloyed metal powders and which have a compressive strength of 20 to 250N and an internal surface area of 10 to 90 m$^2$/g and in which the metal powders contain 60 to 100% by weight of one or more ferrous metals, 0 to 15% by weight of one or more metals of group VIB and 0 to 25% by weight of one or more hydrogenationally inert elements from the group comprising aluminum, silicon, titanium and carbon, all relative to the total weight of the metal powder.

The invention consequently relates to a continuous process for preparing isocamphylcyclohexanols from compounds having the carbon skeleton of the isocamphylguaiacols or isocamphylphenols by hydrogenation with hydrogen at elevated temperature and elevated pressure, which process comprises using as catalysts support-free compacted molded bodies which are produced from metal powders and which have a compressive strength of 20–250N and an internal surface area of 10–90 m$^2$/g and in which the metal powders contain 60–100% by weight of one or more ferrous metals, 0–15% by weight of one or more metals of group VIB and 0–25% by weight of one or more hydrogenationally inert elements from the group comprising aluminum, silicon, titanium and carbon, all relative to the total weight of the metal powder.

DETAILED DESCRIPTION OF THE INVENTION

Compounds having the carbon skeleton of the isocamphylguaiacols or isocamphyl-phenols are to be understood as meaning optionally substituted isocamphyl-guaiacols and isocamphylphenols, alkyl groups, in particular $C_1$–$C_6$-alkyl groups preferably being suitable as substituents.

The metal powders to be used according to the invention may contain the said elements of the ferrous group and also, optionally, of group VIB and, optionally, the hydrogenationally inert elements Al, Si, Ti and C in elemental form or in the form of alloys.

The ferrous subgroup of group VIII of the periodic system (Mendeleyev) contains the elements iron, cobalt and nickel. The support-free molded bodies to be used according to the invention contain one or more of said metals in amounts of at least 60, preferably at least 70, in particular at least 80% by weight, relative to the total weight of the support-free molded bodies.

Group VIB of the periodic system contains the elements chromium, molybdenum and tungsten. The support-free molded bodies to be used according to the invention contain one or more of said metals in amounts of 0–15% by weight. If they are present, the metal powders or alloyed metal powders contain at least 0.1, preferably at least 0.3, in particular, preferably at least 0.5% by weight, relative to the support-free molded bodies; they contain one or more of said metals in amounts of not more than 15, preferably not more than 10 and, in particular, not more than 5% by weight, relative to the support-free molded bodies.

The support-free molded bodies to be used according to the invention contain, in addition—in each case relative to the support-free molded bodies—0 to 25, preferably 0 to 15% by weight of one or more elements from the group comprising aluminum, silicon, titanium and carbon. These elements are hydrogenationally inert under the conditions of the process according to the invention, i.e. they have no catalytic action. According to a preferred embodiment, the support-free molded bodies contain, in addition to the metals of group VIII and, optionally, group VIB, not more than 10% by weight of aluminum and not more than 5% by weight of each of the elements silicon, titanium and carbon.

The support-free molded bodies can be produced by conventional methods by compacting the metal powders or alloyed metal powders on tabletting or pelleting machines under high pressure, in which process graphite in amounts of 0.5–1.5% by weight, relative to the total weight of the constituents forming the catalyst, or adhesives in small amounts may also be used to improve the adhesion of the metal particles. The support-free molded bodies are preferably produced in an oxygen-free atmosphere in order to avoid surface oxidations. Tabletted and pelleted molded bodies having diameters of 3 to 7 mm are the most effective and most beneficial for the conduct of the reaction. The compressive strength of the molded bodies, which has, according to the invention, values of 20 to 250N, preferably 100 to 220N, is of considerable importance. Lower compressive strengths result in disintegration of the molded bodies or erosive abrasion, which would bring about a metallic contamination of the reaction product. Higher values require a disproportionate effort during compaction without further advantages being achieved. The internal surface area of the molded bodies, which according to the invention has values of 10 to 90 $m^2/g$ and is crucial for as quantitative a conversion as possible of the feedstock is furthermore of considerable importance.

The compressive strength of the support-free molded bodies can be determined in accordance with DIN 50 106.

The testing of support-free molded bodies for the required internal surface areas and, consequently, for usability for the process according to the invention can be carried out by methods which have been described by F. M. Nelsen and F. T. Eggertsen, Analyt. Chem. 30 (1958), pages 1387–1390 and S. J. Gregg and K. S. W. Sing. Adsorption, Surface Area and Porosity, London 1982, Chapters 2 and 6.

The hydrogenation reactor may be either a single high-pressure steel or steel-alloy tube completely or partly filled with the support-free molded bodies, in which case the use of support-free molded bodies on trays (wire baskets or the like) may also be useful for certain tube diameters or, alternatively, a sheathed high-pressure tube bundle whose individual tubes are completely or partly filled with support-free molded bodies. Furthermore, instead of a large single tubular reactor, an arrangement of a plurality of small single reactors one behind the other can be operated in cascade.

For the hydrogenation process pure hydrogen precompressed to a pressure of 50–400 bar, preferably 100 to 350 bar, particularly preferably 150–300 bar, is used, in which connection a 10 to 60 times molar, preferably 20 to 40 times molar amount of hydrogen, relative to the stoichiometric amount, is employed.

The hydrogenation is carried out continuously using the fixed-bed process on the support-free molded bodies acting as hydrogenation catalysts in the descending liquid phase or, alternatively, preferably in the rising liquid phase by allowing the solution to be hydrogenated either to flow from below rising in cocurrent together with the previously admixed hydrogen via the catalyst provided in a hydrogenation reactor (cocurrent process) or, alternatively, by feeding the solution to be hydrogenated ascending from below in opposition to the hydrogen flowing in from above (countercurrent process).

The temperature range for the process according to the invention is 140° to 280° C., preferably 180° to 260° C.

In the process according to the invention, a mixture of isomeric isocamphyl-cyclohexanols, such as 2-hydroxy-1-(5-isocamphyl)cyclohexane, 3-hydroxy-1-(5-isocamphyl) cyclohexane, 4-hydroxy-1-(5-isocamphyl)cyclohexane is produced with the aid of the use of the catalysts described from the isocamphylguaiacols or isocamphylphenols used.

In the procedure described, the catalyst loading is 0.05 to 1.0 kg, preferably 0.1 to 0.5 kg of feedstock per liter of catalyst and per hour. The isocamphylgualacols or isocamphylphenols used can be diluted with a suitable solvent which is inert in the reaction, for example aliphatic monoalcohols or cyclohexanols, in an amount of 10 to 100, preferably 10 to 40% by weight, relative to the weight of the feedstock.

After cooling to a temperature of <60° C., the reaction mixture leaving the hydrogenation reactor is let down, in which process the excess hydrogen can be collected and reused after compression and addition of used hydrogen.

Under the reaction conditions described, quite unexpectedly high catalyst service lives of 15,000 hours and over can be achieved in this way, which results in catalyst consumptions of <0.1% by weight, relative to the reaction product obtained.

In contrast to carrier-containing catalysts, the oxygen-free and support-free fixed-bed catalysts to be used according to the invention do not tend to "bleed", i.e. to transfer catalyst constituents in ionic or colloidal form to the solution phase of the substrate so that the substrate is not contaminated with heavy metals which normally can also be removed from the substrate only with difficulty, for example with the aid of ion exchangers. The catalyst metals to be used can readily be worked up, for instance after prolonged use of the catalyst, and reused since the heavy metals do not have to be separated laboriously from a support material.

The reaction products obtained are virtually free of aromatic components.

After hydrogenation without solvent, the isocamphylcyclohexanols can be further processed after distillative removal of any low-boiling components, normally without further purifying process, and in the case of hydrogenation with solvent, after additionally distilling off the solvent. It is, however, also possible to separate and concentrate the isocamphylcyclohexanols obtained distillatively or by other known physical methods of separation.

EXAMPLES

Example 1

A vertical-standing, thermally insulated high-pressure tube made of stainless, acid-resistant steel having an internal diameter of 45 mm and a length of 1 m, which had previously been flushed with nitrogen so as to be oxygen-free, was filled with 1.4 l of a catalyst produced by tabletting a pulverized Ni/Mo/Al alloy having an Mo content of 1.02% by weight and an Al content of 6.1% by weight.

With a cylinder height of 5 mm and a diameter of 5 mm, the tablets had a compressive strength of 210N on the cylinder lateral surface and an internal surface area of 71 $m^2/g$.

Then 180 g per hour of a 38% strength by weight solution of a mixture of isocamphylguaiacols, such as are produced in the alkylation of camphene with guaiacol, were pumped through the high-pressure tube into cyclohexanol together with 1.5 $Nm^3$ of hydrogen under a pressure of 300 bar so as to ascend from the bottom upwards, the mixture to be hydrogenated being heated to a temperature of 190° C. in an upstream, electrically heated heat exchanger before entering the high-pressure tube.

The reaction product leaving the reaction tube was cooled to a temperature of <60° C. in a second heat exchanger (water cooler) under a hydrogen pressure of 300 bar and was separated in a gas separator from excess hydrogen, which was fed back again into the reaction system.

After further cooling to a temperature of <30° C. and letting down to normal pressure, the reaction product was investigated by UV spectroscopy.

It was found that the residual aromatic component was less than 0.1% by weight.

After distilling off the solvent, a glass-clear viscous oil was obtained which contained the isomeric isocamphyl compounds 2-hydroxy-1-(5-isocamphyl)cyclohexane, 3-hydroxy-1-(5-isocamphyl)cyclohexane and 4-hydroxy-1-(5-isocamphyl)cyclohexane in a mixing ratio of approximately 3:1:3 and smelled pleasantly of sandalwood.

After a service life of 5,018 hours, the catalyst was as effective as ever.

Example 2

A vertical-standing thermally insulated high-pressure tube made of stainless, acid-resistant steel having an internal diameter of 45 mm and a length of 1 m, which had previously been flushed with nitrogen so as to be oxygen-free, was filled with 1.4 l of a catalyst produced by tabletting a pulverized Ni/Al alloy having an Al content of 5.8% by weight.

With a cylinder height of 5 mm and a diameter of 5 mm, the tablets had a compressive resistance of 156 N on the cylinder lateral surface and an internal surface area of 69 $m^2/g$.

Through this tube, 170 g of a 38% strength by weight solution of a mixture of isocamphylguaiacols, such as are produced in the alkylation of camphene with guaiacols, were pumped through the high-pressure tube into cyclohexanol together with 1.5 $Nm^3$ of hydrogen under a pressure of 300 bar so as to ascend from the bottom upwards, the mixture to be hydrogenated being heated to a temperature of 195° C. in an upstream, electrically heated heat exchanger before entering the high-pressure tube.

The reaction product leaving the reaction tube was cooled in a second heat exchanger (water cooler) to a temperature of <60° C. under a hydrogen pressure of 300 bar and separated in a gas separator from excess hydrogen, which was fed back again into the reaction system.

After further cooling to a temperature of <30° C. and letting down to normal pressure, the reaction product was investigated by UV spectroscopy.

It was found that the residual aromatic component was less than 0.1% by weight.

After distilling off the solvent, a glass-clear viscous oil was obtained which contained the isomeric isocamphyl compounds 2-hydroxy-1-(5-isocamphyl)cyclohexane, 3-hydroxy-1-(5-isocamphyl)cyclohexane and 4-hydroxy-1-(5-isocamphyl)cyclohexane in a mixing ratio of approximately 3:1:2 and smelt pleasantly of sandalwood.

After a service life of 8,608 hours, the catalyst was as effective as ever.

Example 3

A vertical-standing thermally insulated high-pressure tube made of stainless, steel having an internal diameter of 45 mm and a length of 1 m, was filled with 1.4 l of a catalyst obtained by tabletting a pulverized Ni/Fe alloy.

The alloy contained an Fe component of 15%. With a cylinder height of 5 mm and a diameter of 5 mm, the tablets had a compressive strength of 137N on the cylinder lateral surface and an internal surface area of 74 $m^2/g$.

Then 180 g per hour of a 38% strength by weight solution of a mixture of isocamphylguaiacols, such as are produced in the alkylation of camphene with guaiacol, was pumped through the high-pressure tube into cyclohexanol together with 1.5 $Nm^3$ of hydrogen under a pressure of 300 bar so as to ascend from the bottom upwards, the mixture to be hydrogenated being heated to a temperature of 205° C. in an upstream, electrically heated heat exchanger before entering the high-pressure tube.

The reaction product leaving the reaction tube was cooled in a second heat exchanger (water cooler) to a temperature of <60° C. under a hydrogen pressure of 300 bar and separated in a gas separator from excess hydrogen, which was fed back again into the reaction system.

After further cooling to a temperature of <30° C. and letting down to normal pressure, the reaction product was investigated by UV spectroscopy.

It was found that the residual aromatic component was less than 0.1% by weight.

After distilling off the solvent, a glass-clear viscous oil was obtained which contained the isomeric isocamphyl compounds 2-hydroxy-1-(5-isocamphyl)cyclohexane, 3-hydroxy-1-(5-isocamphyl)cyclohexane and 4-hydroxy-1-(5-isocamphyl)cyclohexane in a mixing ratio of approximately 3:2:3 and smelt pleasantly of sandalwood.

After a service life of 4,100 hours, the catalyst was as effective as ever so that the composition of the reaction product did not alter over this interval of time.

It will be understood that the specification and examples are illustrative but not limitative of the present invention and that other embodiments within the spirit and scope of the invention will suggest themselves to those skilled in the art.

What is claimed is:

1. A process for preparing isocamphylcyclohexanols from isocamphylguaiacol or isocamphylphenol compounds by hydrogenation with hydrogen at elevated temperature and elevated pressure, which comprises using support-free materials which act as catalysts and which are present as compacted molded bodies produced from metal powders which have a compressive strength of 20 to 250N and an internal surface area of 10 to 90 m$^2$/g and in which the metal powders contain 60 to 100% by weight of one or more ferrous metals of Fe, Co or Ni, 0 to 15% by weight of one or more metals of group VIB and 0 to 25% by weight of one or more hydrogenationally inert elements from the group comprising aluminum, silicon, titanium and carbon, all relative to the total weight of the metal powder.

2. A process according to claim 1, wherein the metal powders contain 70 to 100% by weight of one or more ferrous metals.

3. A process according to claim 1, wherein the metal powders have a content of 0.1 to 15% by weight of one or more metals of group VIB.

4. A process according to claim 1, wherein the metal powders have a content of 0 to 10% by weight of aluminum and of 0 to 5% by weight of each of the elements Si, Ti and C.

5. A process according to claim 4, wherein the total content of the elements Al, Si, Ti and C is 0 to 15% by weight.

6. A process according to claim 1, wherein the hydrogen pressure is 5 to 400 bar.

7. A process according to claim 1, wherein the hydrogenation temperature is 140° to 280° C.

8. A process according to claim 1, wherein a 10 to 60 times higher amount of hydrogen, relative to the stoichiometric amount, per mol of starting material is used during the process.

9. A process according to claim 1, wherein stationary disposed catalysts are employed in a continuous descending liquid phase and a catalyst loading of 0.05 to 1.0 kg of starting product per liter of catalyst and per hour is established.

10. A process according to claim 1, wherein the starting material is diluted with 10 to 100% by weight of a solvent which is inert in the reaction, relative to the starting material.

11. A process according to claim 1, wherein the metal powders contain 80 to 100% by weight of one or more ferrous metals.

12. A process according to claim 1, wherein the metal powders have a content of 0.3 to 10% by weight of one or more metals of group VIB.

13. A process according to claim 1 wherein the metal powders have a content of 0.5 to 5% by weight of one or more metals of group VIB.

14. A process according to claim 4, wherein the total content of the elements Al, Si, Ti and C is 0 to 10% by weight.

15. A process according to claim 1, wherein the hydrogen pressure is 100 to 350 bar.

16. A process according to claim 1, wherein the hydrogen pressure is 100 to 300 bar.

17. A process according to claim 1, wherein the hydrogen pressure is 180° to 260° C.

18. A process according to claim 1, wherein a 20 to 40 times higher amount of hydrogen, relative to the stoichiometric amount, per mol of starting material is used during the process.

19. A process according to claim 1, wherein stationary disposed catalysts are employed in a continuous descending liquid phase and a catalyst loading of 0.1 to 0.5 kg of starting material per liter of catalyst and per hour is established.

20. A process according to claim 1, wherein the starting material is diluted with 10 to 40% by weight of a solvent which is inert in the reaction, relative to the starting material.

* * * * *

UNITED STATES PATENT AND TRADEMARK OFFICE
CERTIFICATE OF CORRECTION

PATENT NO : 5,874,648
DATED : February 23, 1999
INVENTOR(S): Darsow, Gerhard

It is certified that error appears in the above-identified patent and that said Letters Patent is hereby corrected as shown below:

Col. 8, line 4    Delete " product " and substitute -- material --

Signed and Sealed this

Second Day of November, 1999

Attest:

Q. TODD DICKINSON

Attesting Officer    Acting Commissioner of Patents and Trademarks